(12) United States Patent
Atkinson et al.

(10) Patent No.: US 7,198,708 B2
(45) Date of Patent: Apr. 3, 2007

(54) ELECTROCHEMICAL BIOSENSOR

(75) Inventors: Anne Louise Atkinson, Milton Keynes (GB); Brian Jeffrey Birch, Higham Ferrers (GB); Robert Andrew Porter, Rushden (GB)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 717 days.

(21) Appl. No.: 10/457,202

(22) Filed: Jun. 9, 2003

(65) Prior Publication Data

US 2004/0026266 A1   Feb. 12, 2004

(30) Foreign Application Priority Data

Jun. 10, 2002 (EP) ................... 02254022

(51) Int. Cl.
*G01N 27/327* (2006.01)

(52) U.S. Cl. ............... 205/787; 205/792; 204/403.01

(58) Field of Classification Search ............... 204/403.01–403.15, 416–418; 205/777.5, 205/787, 792
See application file for complete search history.

(56) References Cited

U.S. PATENT DOCUMENTS

| | | | |
|---|---|---|---|
| 3,847,777 A | 11/1974 | Haddad et al. | 204/415 |
| 4,627,906 A | 12/1986 | Gough | 204/415 |
| 4,795,452 A | 1/1989 | Blaney et al. | 604/385.27 |
| 4,795,542 A | 1/1989 | Ross et al. | 204/403.09 |
| 5,723,345 A * | 3/1998 | Yamauchi et al. | 436/518 |
| 5,746,898 A | 5/1998 | Preidel | 204/403.09 |
| 6,054,039 A * | 4/2000 | Shieh | 205/778 |
| 6,758,922 B2 * | 7/2004 | Hamilton | 149/75 |
| 7,051,375 B2 * | 5/2006 | Polak et al. | 2/82 |

FOREIGN PATENT DOCUMENTS

| | | |
|---|---|---|
| GB | 1 554 292 | 10/1979 |
| WO | 93/13408 | 7/1993 |

OTHER PUBLICATIONS

Table of Solid Surface Energies downloaded from www.accudynetest.com/surface_energy_materials.html on Jul. 17, 2006.*
CAPLUS abstract of Sirko ("Polarographic determination of glutathione," Izvestiya Vysshikh Ucehebnykh Zavedenii, Pischevaya Tekhnologiya (1979), (6), 118-119).*

(Continued)

*Primary Examiner*—Alex Noguerola
(74) *Attorney, Agent, or Firm*—Michael P. Aronson

(57) ABSTRACT

An electrochemical biosensor for quantifying one or more redox species in a liquid sample comprising a background electrochemical activity, wherein said biosensor comprises:
(i) an electrode system;
(ii) a filter means comprising a sample loading position; and
(iii) a charge transfer surface between said filter means and said electrode system;
wherein said filter means separates said sample loading position from said charge transfer surface by an amount of filter material capable of providing a tangential peak height for said background electrochemical activity of less than 30% of the tangential peak height for said redox species; and said biosensor comprises an intermediate layer between said filter means and said charge transfer surface, wherein said intermediate layer has a lower energy requirement to transfer said liquid sample to said charge transfer surface than said filter material.

11 Claims, 10 Drawing Sheets

OTHER PUBLICATIONS

CAPLUS abstract of Bezerra de Carvalho Junior et al. ("An enzymic and polarographic estimation of vitamin C using ascorbate oxidase," Cicencia e Cultura (Sao Paulo) (1982), 34(11), 1482-4).*

CAPLUS abstract of Wring et al. ("Voltammetric behavior of screen-printed carbon electrodes, chemically modified with selected mediators, and their application as sensors for the determination of reduced glutathione," Analyst (Cambridge, United Kingdom) (1991), 116(2), 123-9).*

CAPLUS abstract of Raj et al. ("Electroanalytical applications of cationic self-assembled monolayers: square-wave voltammetric determination of dopamine and ascorbate," bioelectrochemistry (2001), 53(2), 183-191).*

European Search Report No. EP 02 25 4022 dated Nov. 26, 2002, 3 pp.

International Search Report No. PCT/EP 03/05458 dated Aug. 21, 2003, 3 pp.

* cited by examiner

ELECTROCHEMICAL BIOSENSOR

FIELD OF THE INVENTION

The present invention relates to the field of electrochemical biosensors for the quantification of a redox species in a biological sample.

BACKGROUND TO THE INVENTION

Redox species have inherent electrochemical activity and are therefore capable of exchanging electrons directly with a working electrode to produce an electrochemical signal. This allows direct electrochemical detection and quantification without a requirement for a mediator means, such as via an enzyme mediated reaction.

The quantification of redox species in the prior art has had to rely on laboratory based analytical techniques such as High Pressure Liquid Chromatography (HPLC) attached to a detector comprising a series of porous electrodes at different potentials (CoulArray™). While this system is suitably accurate, the size and expense of the equipment render it unsuitable for large scale sample testing or in-home consumer usage. Furthermore, biological samples must commonly undergo extensive pre-treatment to provide them in a form that can be analysed by HPLC.

With these matters in mind it would be dearly desirable to develop a means of quantifying redox species which is not only accurate, but is also conveniently portable, disposable and able to analyse a biological sample which has undergone minimal pre-treatment.

Portable disposable biosensors of the prior art are not capable of accurately quantifying redox species at their naturally occurring levels in a biological sample. The redox species in enzyme mediated biosensors, such as ferricyanide ions released in standard glucose biosensors, are produced in abundance and easily quantifiable. In contrast the concentration of any individual redox species naturally present in a biological sample is comparatively low, making the accurate quantification of the electrochemical signal due to any individual spedes by conventional biosensors impossible.

The concentrations at which redox species are present in biological samples also renders background electrochemical activity from interferents, such as proteins, a particular problem. The magnitude of the electrochemical signal from the interferent commonly masks or skews the electrochemical signal of the redox species for which detection is sought. Conventional biosensors have no means of adequately making the distinction between interferent electrochemical activity and that of a particular redox species under analysis.

The present invention therefore aims to provide a disposable electrochemical biosensor which can accurately quantify redox species in a biological liquid sample.

A number of redox sensors are known which utilise an enzyme mediator to generate the redox species to be detected by enzymatic reaction with a component in the sample. These are disclosed in U.S. Pat. No. 4,795,452, GB-A-1 554 292, U.S. Pat. No. 5,746,898 and WO-A-93/13408. The latter document discloses a system in which a liquid/solid interface is provided with the electrodes by virtue of a liquid sample filling a well. U.S. Pat. No. 3,847,777 discloses a gas sensor in which a wet electrolyte system is used to interface with the electrodes. For simple and cost effective manufacture of an electrochemical system usable in the home, there is a need to provide a system which does not rely on an enzymatic mediator or a wet electrode arrangement. However, such a system would still need a filter to reduce interferents yet be capable of wetting the electrodes.

SUMMARY OF THE INVENTION

In order to solve the above defined problem, the present invention provides a consumer operable electrochemical biosensor which can accurately quantify redox species when present at micromolar levels in a biological liquid sample comprising one or more electrochemical interferents. In contrast conventional consumer devices have only allowed quantification at millimolar concentrations.

Therefore, in a first aspect, the present invention provides an electrochemical biosensor for quantifying one or more redox species in a liquid sample comprising a background electrochemical activity, wherein said biosensor comprises:
 (i) an electrode system;
 (ii) a filter means comprising a sample loading position; and
 (iii) a charge transfer surface between said filter means and said electrode system;

wherein said filter means separates said sample loading position from said charge transfer surface by an amount of filter material capable of providing a tangential peak height for said background electrochemical activity of less than 30% of the tangential peak height for said redox species; and said biosensor further comprises an intermediate layer between said filter means and said charge transfer surface, wherein said intermediate layer has a lower energy requirement to transfer said liquid sample to said charge transfer surface than said filter material.

In a first embodiment the invention relates to an electrochemical biosensor as described above wherein said filter material is selected from the group comprising synthetic membranes, nitrocellulose, cellulose, silica, filter paper and agar gel.

The biosensor comprises an intermediate layer between said filter means and said charge transfer surface, wherein said intermediate layer has a lower energy requirement to transfer said liquid sample to said charge transfer surface than said filter material. In other words, there is a lower energy of wetting between the intermediate layer and the electrode system than there would be if there were direct contact between the filter means and the electrodes.

The intermediate layer may be regarded as a matrix capable of forming a transfer layer when wetted by the liquid sample and thus the intermediate layer can be provided dry before use, ie to be wetted by the liquid sample which contains the redox species to be detected, unlike a system where an enzyme or other mediator is used to generate the redox species.

In a most preferred embodiment said transfer layer comprises cellulose as this has been found to be particularly effective in achieving uniform wetting of the electrode.

It is recognised that an electrochemical biosensor according to the invention may be used in conjunction with a separate device that is capable of measuring the electrochemical signals generated by the electrode systems however in a preferred embodiment the invention provides a electrochemical biosensor integrally comprising a means for measuring an electrochemical signal.

An electrochemical biosensor in accordance with the above description is potentially suitable for quantification of any redox species. However, for individual measurements to be made for specific redox species the biosensor is accompanied by directions for its usage. A further embodiment of the invention therefore provides an electrochemical biosensor as described above further comprising a means for directing the usage of said biosensor within one or more predetermined parameters for quantification of said one or more redox species.

A second object of the invention provides for the use of an electrochemical biosensor in accordance with the above description in the quantification of a redox species.

In a preferred embodiment the invention related to the use of a electrochemical biosensor as described above wherein said redox species is either ascorbate or reduced glutathione.

Tests and Definitions

The expression "disposable" is used herein to indicate capacity for a single measurement usage.

For the purpose of the present invention a "redox species" refers to an electrochemically active analyte comprising a moiety capable of electrochemical oxidation and/or reduction at an electrode (wherein oxidation gives a positive current and reduction gives a negative current) within the operating range of standard, accumulation and stripping electrochemical techniques. Preferably such electrochemical techniques are within the operating window of +/−2 volts.

A liquid sample is taken to comprise any liquid sample comprising components having a biological origin, preferably a biological liquid sample will comprise plant or animal derived materials in the form of a plant or animal extract. Most preferably a biological liquid sample will comprise one or more components of human origin derived from or comprising fluids selected from the group comprising sweat, saliva, blood, tears and urine.

An electrochemical interferent is defined as comprising an electroactive moiety other than the redox species for which quantification is sought which achieves an electrochemical reaction at the electrode at a similar potential as said redox species i.e. approx. +/−1 volt, and therefore masks or skews the electrochemical signal thereof.

For the purpose of the present invention the tangential height of a peak is provided by calculating the difference between successive data points (i) of 2 mV as one moves along the voltage axis of a linear sweep voltammetry curve; the increment at which that difference changes from negative to positive provides a first tangent; the curve peak is defined as the mid-point of the increment where the difference between successive data points is zero; a second tangent is provided by the increment following the peak where the difference between successive data points again changes from negative to positive. The tangential peak height is then defined as the length of a line, perpendicular with respect to the V axis, from the peak to point of intersection with a second line which links the first and second tangents as defined here above.

For a positive going REDOX signal, at either side of the signal maximum for the REDOX species of interest, two points may be defined either at the adjacent minima or at points of inflexion. Typically the inflexion from zero to positive gradient may define the first point and the change from negative to zero gradient then defines the second. A tangent can then be constructed between these two points and the vertical height of the maximum calculated from it. The redox signal curve may be defined by a series of observations of measured current at a series of potential steps or from a mathematical fit from the measured data.

For a negative going signal, the definitions are inverted (eg as shown for glutathione in FIG. 5 of the accompanying drawings), where the 'peak' signal is defined by a minima and the two adjacent maxima or points of inflexion may be defined typically by transitions firstly from zero to negative gradient and secondly by positive to zero gradient. Examples are shown in FIGS. 3, 5 and 11 of the accompanying drawings and are described further hereinbelow.

DETAILED DESCRIPTION OF THE INVENTION

The biosensor device of the present invention is provided with a filter means to reduce the level of interferents in the liquid sample supplied to the charge transfer surface such that the electrochemical signal of the redox species for which quantification is sought can be distinguished from that of background interferent electrochemical activity. The liquid sample is loaded at the loading position and as it passes though the filter means by one or more processes comprising capillary action, pump assisted action, and electrophoresis interferents are absorbed by the filter and thus at least partially removed from the sample.

For the purpose of the present invention particular attention is directed to a device which overcomes the associated problem of interferents with strong electrochemistry such as proteins and paracetamol.

The electrochemistry of ascorbate in the absence of an electrochemical interferent typically gives a current peak that appears at 0.2V at pH 7 and this current increases monotonically at the same potential and pH with increasing concentration of ascorbate (changes of one pH unit alters the peak potential by +/−58 mV as in normal Nerstian relationship.) Where the liquid sample to be analysed is derived from a matrix which comprises protein, a broad electrochemical signal peak is observed from 0.5 to 0.6V. Where the protein presence is particularly high, such as where the liquid sample is blood, the magnitude of the protein peak would mask the electrochemical signal corresponding to the ascorbate redox species when assessed by conventional electrochemical biosensors. This effect has been avoided by the device of the present invention through at least the partial removal of such proteins from the liquid sample by the filter means prior to their arrival at the charge transfer surface.

Where a liquid sample comprises electrochemical interferents in the form of proteins, the filter means preferably comprises an amount of filter material selected from one or more of the group comprising, synthetic membrances, nitrocellulose, cellulose, silica, chemically modified silicas, filter paper, agar gel and other materials known in the art for chromatographic binding of proteins.

Silicas with bonded organic chains which attach to hydrophobic molecules such as proteins are also particularly suitable for removal of interferents and therefore appropriately applied as the filter means. Such a material is commercially available as seppacks™. In a particularly preferred embodiment wherein a liquid sample comprises a protein interferent, said filter means comprises from 3 to 5 mg silica per ml of sample, more preferably 3.5 to 4.5 mg/ml, most preferably about 4 mg/ml.

Alternatively or in addition specific binding molecules such as protein A or protein specific antibodies may be used where the removal of a particular interferent is sought.

The amount and specific type of material most suited to adequately remove interferents from a particular liquid sample will depend on the sample to be tested and the nature and abundance of the interferents therein.

Preferably the amount of filter means will be capable of providing a tangential peak height for the electrochemical activity from the interferents of less than 30% of the tangential peak height for said redox species; more preferred less than 25%, further preferred less than 15%, most preferred the amount of filter means will be capable of providing a tangential peak height for the electrochemical activity from the interferents of less than 5% of the tangential peak height for said redox species. Ideally the amount of filter means will be capable of entirely removing electrochemical activity from the liquid sample which is associated with interfering species.

The filter means may also or alternatively comprise means for pH alteration of the liquid sample as this will affect the potential at which the redox reaction will occur and also can be used to increase electroactivity of a particular redox species. The filter means and/or liquid sample may be provided with a further means for the generation hydrogen ions as these enhance oxidation conditions for a particular redox species. Preferably the pH within the filter means will be less than pH 7, more preferably less than pH 5, most preferably about pH 4. This can be achieved by adding to the support structure of the filter or to the liquid sample acids in suitable combination with their salts to create buffer medium.

The passage of the liquid sample to the electrode and the provision of uniform wetting at the electrode surface are required to create the charge transfer surface that will allow accurate quantification of a redox species. This will require favourable interfacial surface energies to drive liquid movement towards the electrode surface, wherein work done must be favourable to the transfer of the liquid sample from the filter to the electrode in order for the required wetting of the electrode to occur.

The favourability towards the movement of the liquid sample from the filter to the electrode surface can be enhanced by the introduction of a intermediate layer between the filter and the electrode surface, wherein said intermediate layer loaded with the liquid sample has a lower transfer energy than the filter loaded with the same liquid sample. The various forces act according to the formula;

work done=$Y_{ps}+Y_{pl}-Y_{ls}$ wherein, $Y_{ps}$ is surface energy between the filter and the intermediate layer, $Y_{pl}$ is the transfer energy required to separate the liquid from the intermediate layer; $Y_{ls}$ is the transfer energy required to separate the liquid from the filter material.

The volume of the intermediate layer will also influence the transfer of the liquid sample to the electrode surface. The volume of the intermediate layer is preferably provided according to the formula:

$$i = \frac{nFD^{o}c}{x}A,$$

where i is the current (amps), n is the number of electrons in oxidation/reduction, F is faradays constant (amps.sec), $D^{o}$ is the diffusion coefficient ($cm^2$/sec) of the redox species, c is the concentration of sample (moles/$cm^3$), x is the distance from the surface of the liquid sample delivered by the filter means to the surface of electrode (cm) and A is the area of the electrode ($cm^2$).

Distance x is suitably in the range from 0 to 500 μm, preferably less than 100 μm, more preferably less than 10 μm. Suitably this intermediate layer comprises cellulose and may act as both a wetting layer and a separating layer. An embodiment of the invention therefore comprises a biosensor as described above wherein said filter means comprises a cellulose layer at said charge transfer surface.

Alternatively or in addition the electron acceptor may comprise one or more protrusions which extend into the filter means or transfer layer in order to reduce distance x, thereby facilitating the movement of the liquid sample to the electrode surface and improving charge transfer.

In a most preferred embodiment movement of the liquid sample to the achieve uniform wetting of the electrode surface can be provided in the absence of an intermediate layer i.e. when distance x is zero. This can be achieved by applying the electrode system directly to the filter material to provide intimate contact therewith.

It has been found that a electrode which is made from dried carbon ink and which is in intimate contact directly with the filter material (i.e. when x equals zero) is particularly effective for the quantification of ascorbate in a liquid sample without the need for an intermediate layer. A suitable carbon ink for this purpose is D14 available from G-E-M, Pontypool, Gwent.

To achieve such intimate contact the carbon electrode can suitably be screen printed directly onto a filter material such as nitrocellulose. This provides an effident and effective way of arriving at an electrode according to this embodiment.

Measurement electrode systems for construction of a biosensor according to the present invention, preferably comprise noble metals, most preferably the electrode comprises one or more elements selected from the group comprising gold, platinum, radium, palladium, rhenium and carbon.

The electrode structure preferably comprises a working electrode, a counter electrode and a reference electrode, however it is recognised that the reference and counter electrodes may be combined in some circumstances e.g. when the measurement of current is small (~pα).

The counter electrode should be of sufficient size in relation to the working electrode so that the electrochemical reaction at the charge transfer interface is not limited. Preferably the counter electrode is at least 5 times the size of the working electrode, more preferably at least 10 times the size.

For detection of some redox species the electrochemical reaction at the charge transfer interface requires a mediator. This mediator may be deposited onto the electrode surface, included within the electrode or added to the test sample. Mediators may suitably be selected from the group comprising ferrocyanide, ferricyanide, ferrocene, ferrocene carboxylic acid and cobalt phthalocyanine.

Redox species for the purpose of the present invention are preferably selected from the group of vitamins comprising ascorbate, vitamin E and B vitamins; antioxidant nutrients selected from the group comprising reduced glutathione, polphenols, catechols, flavones such a quecetin, isoflavones such as phytoestrogens; heteroaromatic compounds such as penicillin, aspirin, carbazole, murranes; aromatics such as phenols, carbonyls and benzoates; trace metal ions selected from the group comprising nickel, copper, cadmium, iron and mercury.

In a most prefered embodiment the redox species is ascorbate or reduced glutathione as these are good indicators of human health.

Measurement for the purpose of quantification is suitably performed by a potentiostat. This may comprise a device into which the biosensor as described above is inserted for a reading to be taken or more alternatively may be built into the disposable device provided to the consumer.

Before an electrochemical biosensor constructed in accordance with above description can be used for accurate quantification of a specific redox species biosensors according to a particular embodiment or batch of manufacture must be optmised and calibrated for that specific redox species. This exercise predetermines a range of parameters which can be conveyed for the correct usage of the device.

Data conveyed by the means directing correct usage of the device for detection of one or more particular redox species should comprise a means for conveying assay calibration data for said one or more redox species preferably by means of assay curve parameters.

Data conveyed to the device may also comprise one or more of the following; potential points, (start potential, reference potential, peak potential, sweep range, voltage step intervals and time steps, number of cydes); the nature of the analysis i.e. linear sweep, pulse voltammetry or coulomb configurations; system sensitivity; signal extraction parameters; assay calibration data selected from the group comprising analytical range, clinical range of interest, clinical decision points and assay curve parameters and mathematics to convert signals into concentration of the analyte; error detection parameters.

Optimisation of a biosensor according to the above description may comprise;
(i) identifying the potential at which an electrochemical signal for said specific redox species can be detected with said biosensor;
(ii) calibrating said electrochemical signal.

This process has been undertaken in the present invention with a HPLC device attached to a plurality of porous electrodes arranged in series at different potentials. A suitable electrode arrangement is available under the trademark CoulArray™. When the potential is achieved for the electrochemical reaction between the redox species and the measurement electrode a current flows at the electrode and a corresponding signal is recorded on a chart. By comparison with signals corresponding to liquid samples containing redox species of known concentration the concentration of the redox species in the test sample can be determined.

The test sample is therefore taken and divided into two portions. One of these portions is taken and the redox profile determined using the HPLC-CoulArray™ system.

The second portion is measured using the biosensor provided herein at the potential identified by the HPLC-CoulArray™ system as allowing the electrochemical reaction to proceed, using the same reference electrode. This gives a current reading that can be related to concentration and which should equal the concentration derived from the HPLC-CoulArray™ analysis.

To check this value is due to the analyte to be measured, the sample is spiked with increasing known concentrations of the analyte and a number of readings taken at these different concentrations. A graph of analyte concentration against current can be plotted and the concentration value of the starting material can be extrapolated from the graph. If this value matches the value of the HPLC-CoulArray™ then confidence of the embodiment for that redox species is proven.

Having identified the potential at which a certain redox species will be detected and calibrated a particular biosensor design, provided in accordance with an embodiment described above, further biosensors according to that same design can be provided with dear instructions for their use in the detection of a particular redox species at the identified potential.

EXAMPLE 1

Biosensor for the Analysis of Ascorbate in Urine

Synthetic urine (Alltech) was prepared according to the manufacturer's instructions to produce a dear liquid pH 4.3. Aliquots (10 ml) were placed in glass vials and stirred prior to and for 10 secs following immersion of the biosensor (D14 for ascorbate). Linear sweep (LS) voltammetry was performed on the neat urine and following spiking with stock solution of ascorbate.

Figure 1:
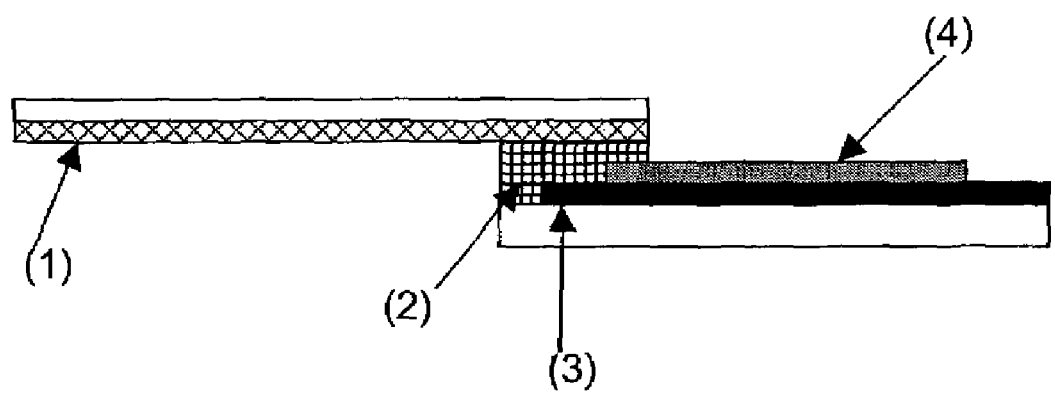
FIGS. 1 and 2: illustrate preferred embodiments of the biosensor according to the present invention, wherein the filter means onto which the liquid sample can be loaded is indicated at (1) and (10); the electrode is illustrated at (3) and (11); and an insulating layer is provided at (4) and (12). In the embodiment of FIG. 1 the charge transfer surface comprises intermediate layer (2).
Figure 2:
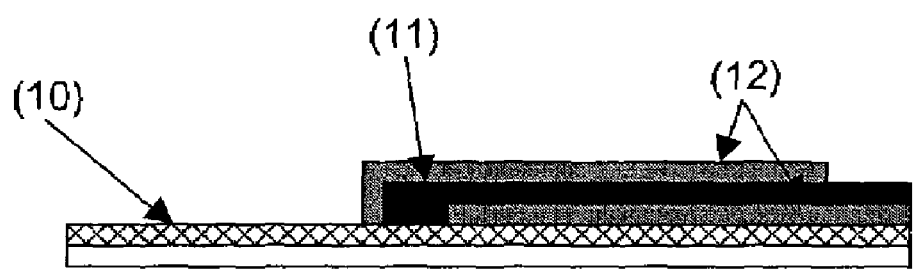
Figure 3:
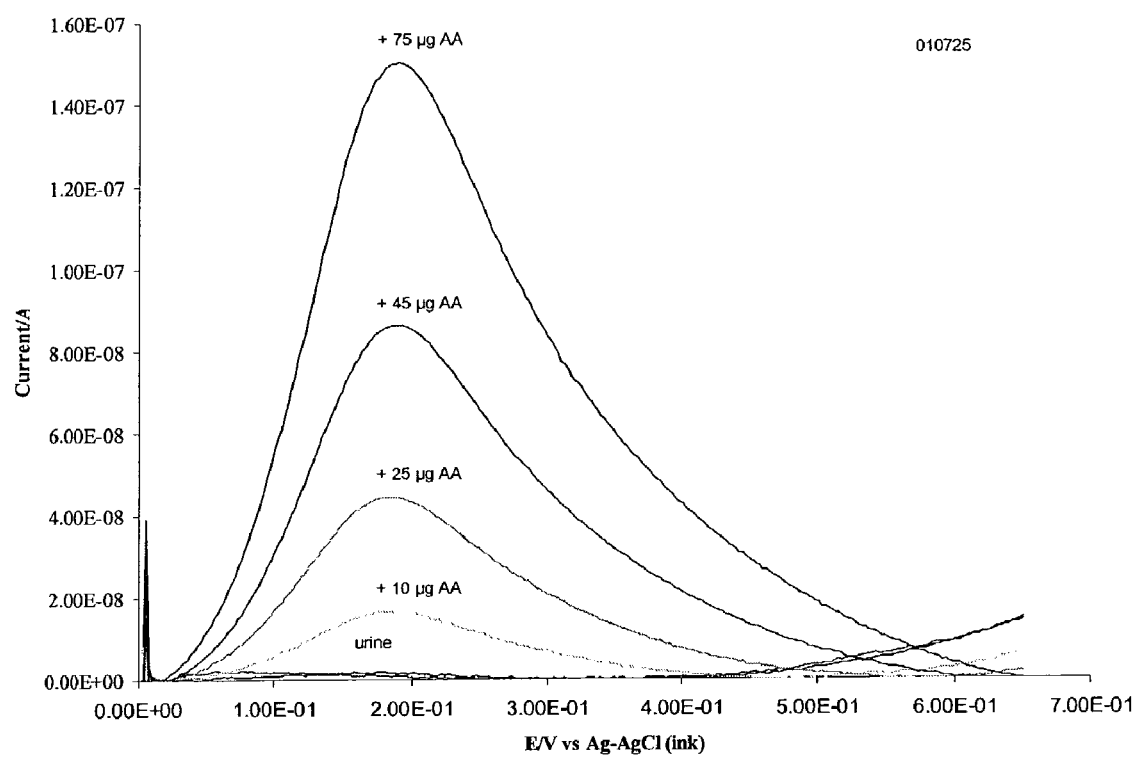
FIG. 3: illustrates an analysis of ascorbate in neat synthetic urine on carbon D14 by linear sweep voltammetry from +0.6 to 0V.
Figure 4:
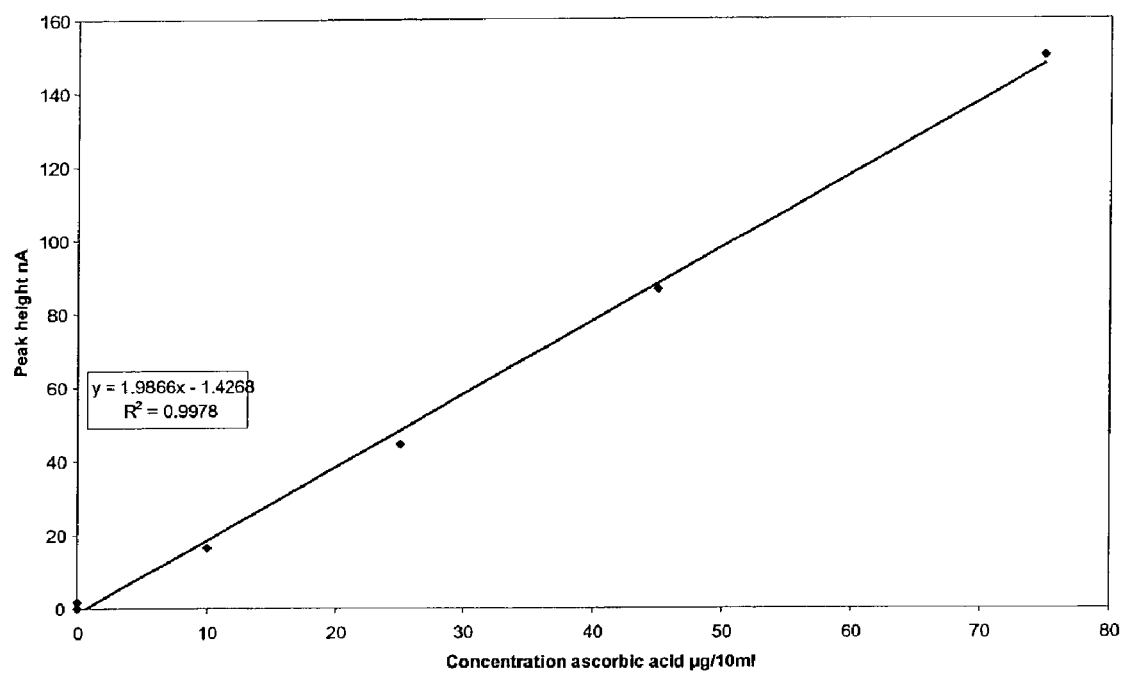
FIG. 4: shows a calibration curve of peak height versus ascorbate concentration for spiked synthetic urine.

No ascorbate was detected in the neat synthetic urine. This was expected since this was not listed in the components of the urine. LS voltammetry of the neat urine showed that there was no apparent interference from electrochemical species within the potential window (+0.2 to +0.4V) characteristic for the presence of ascorbate. This was confirmed by spiking the neat urine with ascorbate (FIG. 3). Oxidation peaks appeared within the predicted potential window and the peak height increased with increasing concentration of analyte (FIG. 4).

Urine is therefore an acceptable matrix for the analysis of ascorbate using the electrochemical biosensor of the present invention.

EXAMPLE 2

Biosensor for the Analysis of Reduced Glutathione (GSH) in Urine

Figure 5:
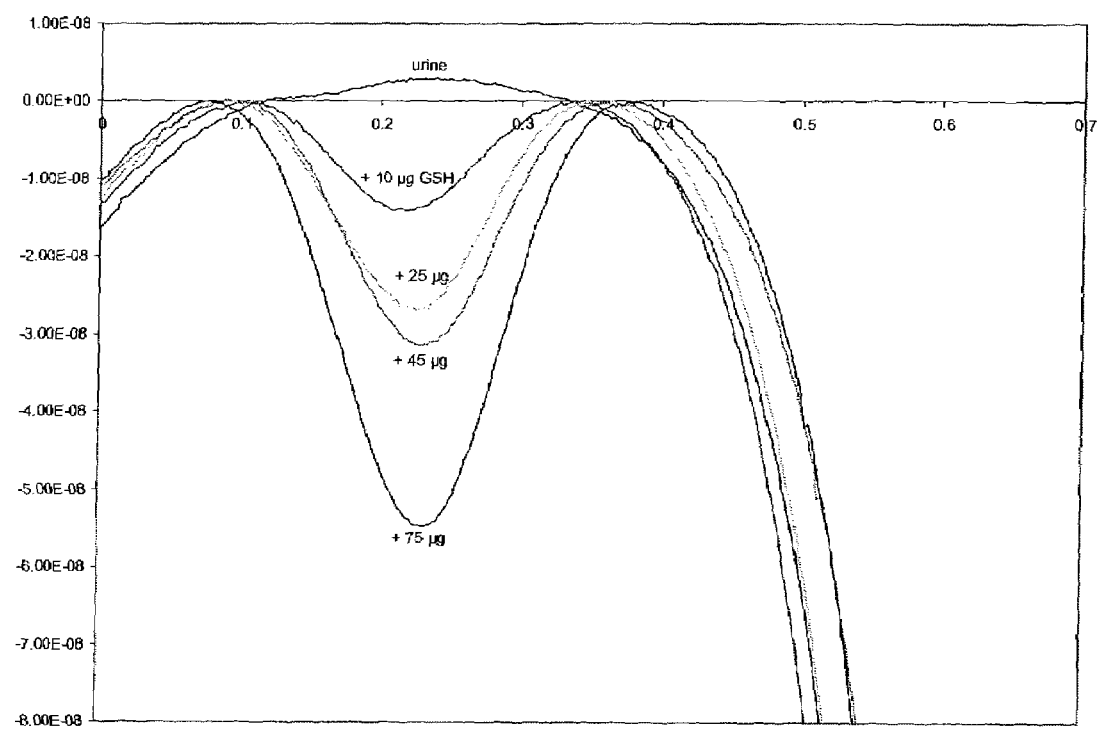
FIG. 5: illustrates an analysis of reduced glutathione (GSH) in neat synthetic urine on a carbon D14/CoPC electrode by differential pulse voltammetry.
Figure 6:
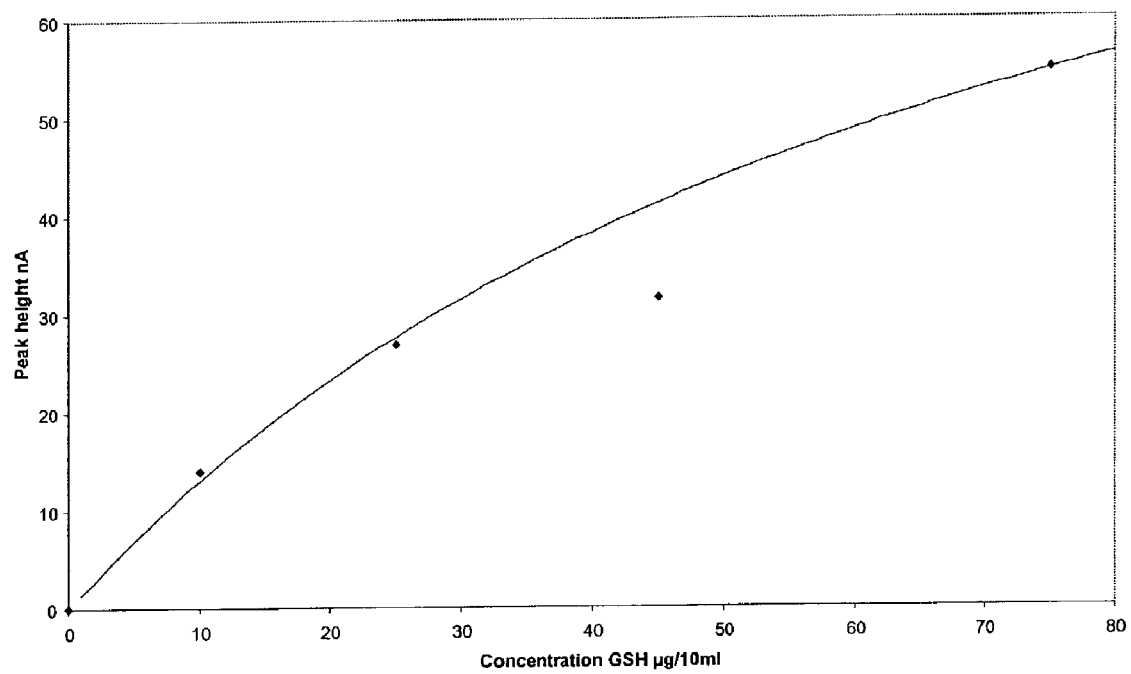
FIG. 6: shows a calibration curve of peak height versus concentration of GSH for spiked synthetic urine samples.

The method of example 1 was repeated with an similar carbon D14 electrode however in this instance comprising overlay of a cobalt phthalocyanine catalyst. Differential pulse (DP) voltammetry was performed on the neat synthetic urine and following spiking with a stock solution of GSH. As expected from the component list no GSH was detected in the neat urine. DP voltammetry of the neat urine showed that there was no apparent interference from electrochemical species within the potential window (+0.2 to +0.4V) which is characteristic for the presence of GSH. This was confirmed by spiking the neat urine with GSH (FIG. 5). Oxidation peaks appeared within the predicted potential window at pH 4 and the peak height increased with increasing concentration of analyte (FIG. 6). The limit of detection was 1.62 µM.

EXAMPLE 3

Analysis of Ascorbic Acid in Urine Using Biosensor with Electrode Nitrocellulose Filter Means Comprising a Cellulose Transfer Layer.

The exposed counter, working and reference electrodes of the D14 sensors were coated with a 100 um layer of 20% cellulose (w/v). A strip of nitrocellulose (8 cm by 1 cm) was placed over the cellulose layer such that the nitrocellulose surface was in direct contact with the cellulose layer and the length of the nitrocellulose strip protruded at least 4 cm below the end of the sensor and 0.5 cm above the reference electrode. The nitrocellulose strip was secured to the electrode with adhesive tape.

The nitrocellulose strip protruding from the electrode-cellulos-nitrocellulose construct was dipped into a urine sample to a depth of 1 cm. The sensor was connected to the electrochemical station but the measurement was delayed until the nitrocellulose layer was wetted to above the height of the reference electrode.

Figure 7A:
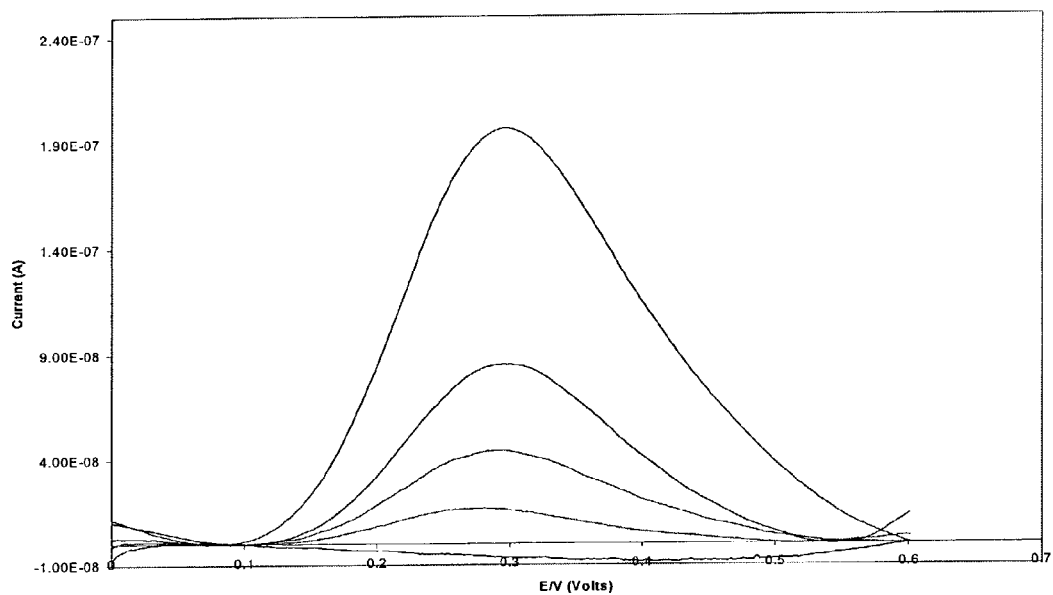
FIG. 7a: illustrates an analysis of ascorbate in synthetic urine using D14/cellulose/nitrocellulose construct.
Figure 7B:
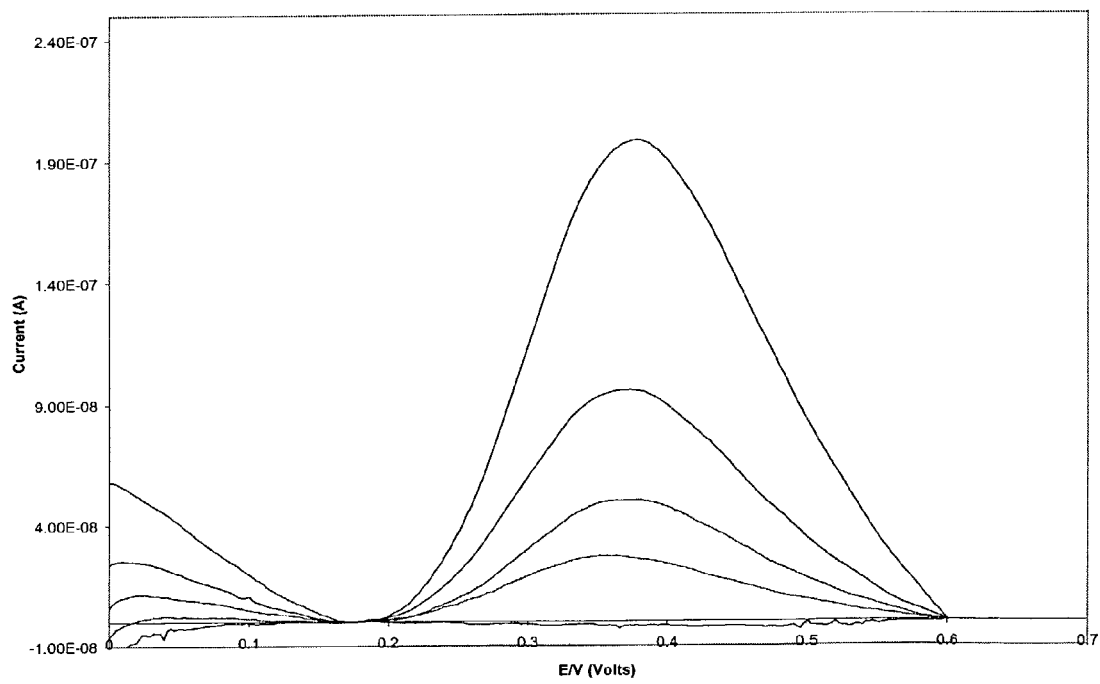
FIG. 7b: illustrates analysis of ascorbate in McIlvaine buffer pH 4 using a D14/cellulose/nitrocellulose construct.
Figure 8:
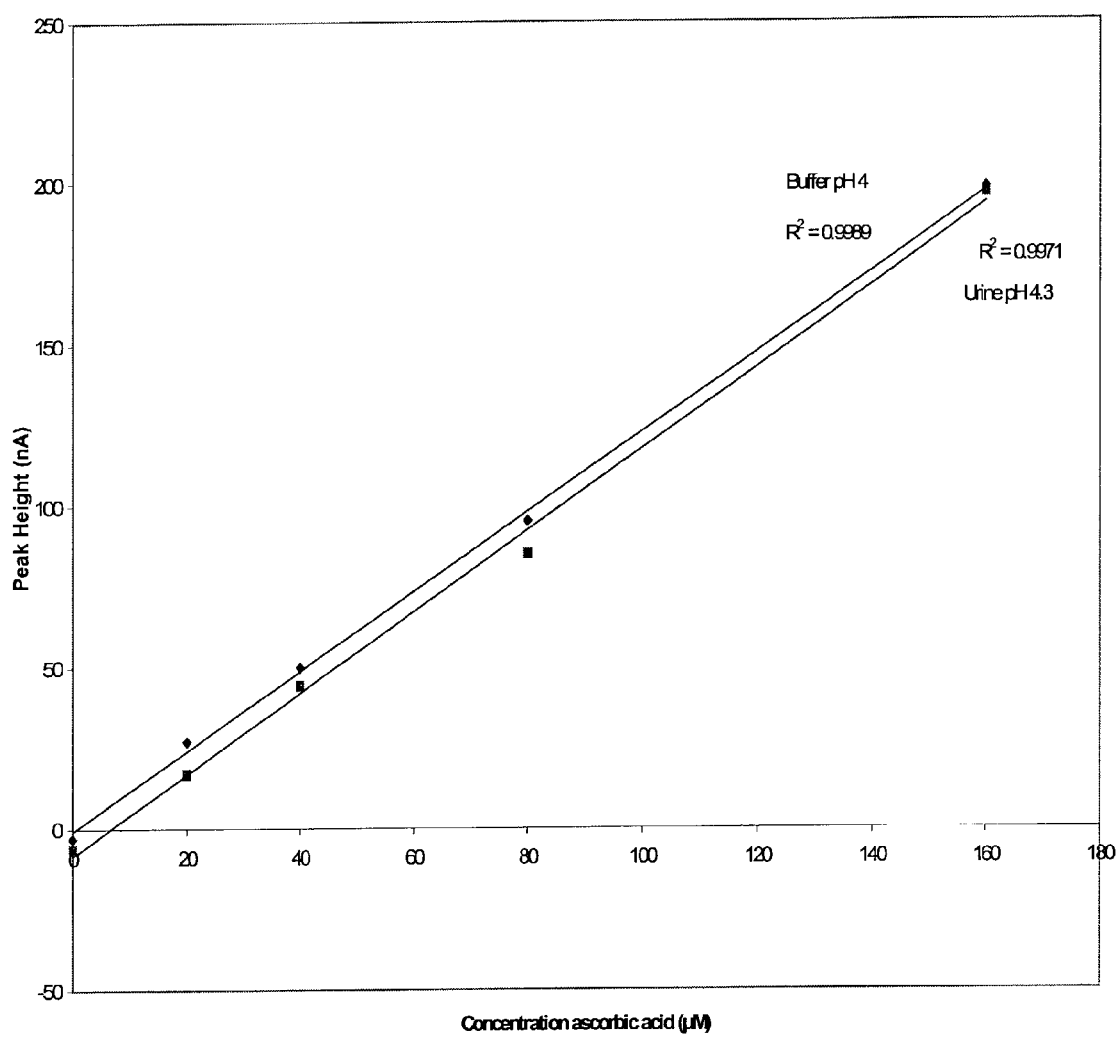
FIG. 8: shows a calibration curve of peak height versus concentration of ascorbate for spike synthetic urine.

Results shown in FIGS. 7 and 8.

EXAMPLE 4

Analysis of GSH in Fish Extract

Aqueous extracts were obtained from individual thawed Hoki samples (8 to 10 g) by immersing in 10 ml perchloric add/boric acid/EDTA buffer (pH less than 1), mashing with a metal spatula. The aqueous supernatant was removed, and silica (5 µm; linked to C12-16 hydrocarbon residues) was added at a concentration of 40 mg/ml supernatant. The aliquots were centrifuged and the supernatant transferred to a vial for electrochemical monitoring. Alternatively, the samples were analysed in the presence of silica following a 1:10 dilution (v/v) in buffer.

Figure 9:
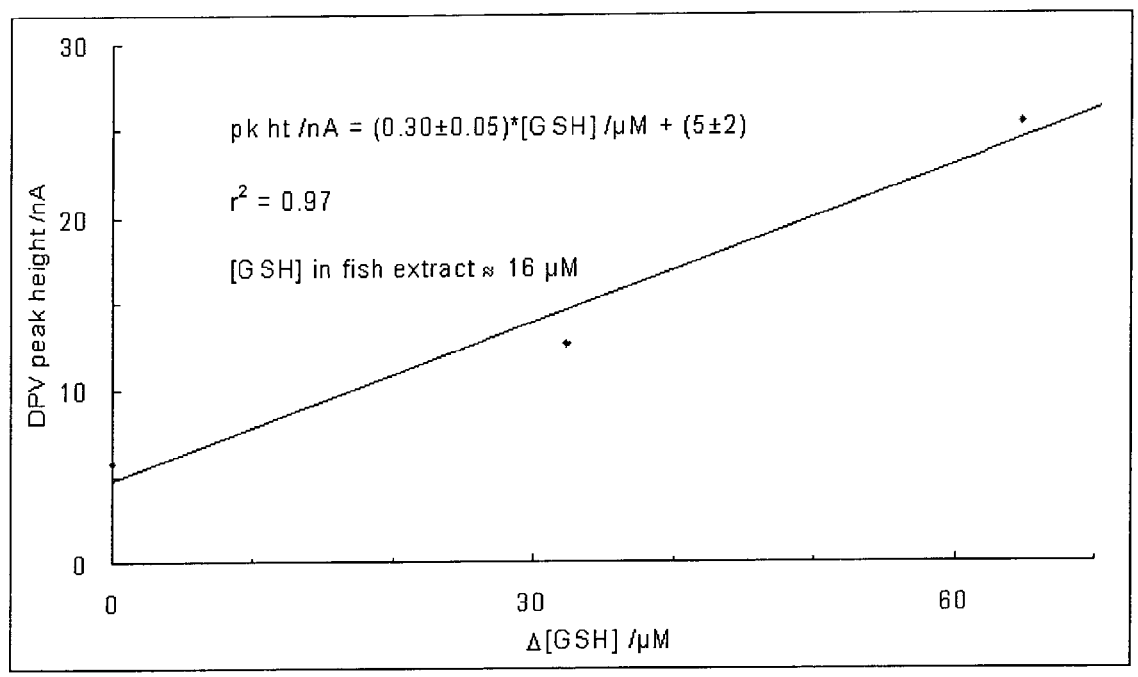
FIG. 9: shows a calibration curve of peak height versus concentration of GSH of spiked fish extract.

Aliquots of the extract were spiked with known concentrations of GSH and monitored with DPV. The concentration of the GSH in the neat extract extrapolated from the graph of electrode response peak height to spiked GSH concentration provided a result of 16 µM. FIG. 9 shows the peak height versus spiked GSH concentration in the fish extract.

EXAMPLE 5

Analysis of Ascorbate in Chopped Tomato:

Samples of chopped tomatoes were obtained, frozen, from Unilever and stored at −24° C. until required. Portions (up to 10 g) of frozen tomato were thawed at room temperature for up to 1 hour prior to analysis. An aliquot (1 g) of thawed tomato was added to McIlvaine buffer pH 4 to give a final volume of 10 ml. The mixture was stirred for 5 minutes.

Protein removal using silica: An aliquot of tomato/buffer mixture (1 ml) was removed and silica (35 mg; 5 µm, C16 bonded) was added. The mixture was whirlimixed and then transferred in total to McIlvaine buffer pH 4 (9 ml) for analysis. The sample was stirred for 10 seconds following immersion of the electrode (D14 for ascorbate; CoPC/D14 for GSH). Voltammograms (linear sweep for AA; differential pulse voltammetry for GSH) were recorded within 1 minute of ceasing stirring.

Figure 10:
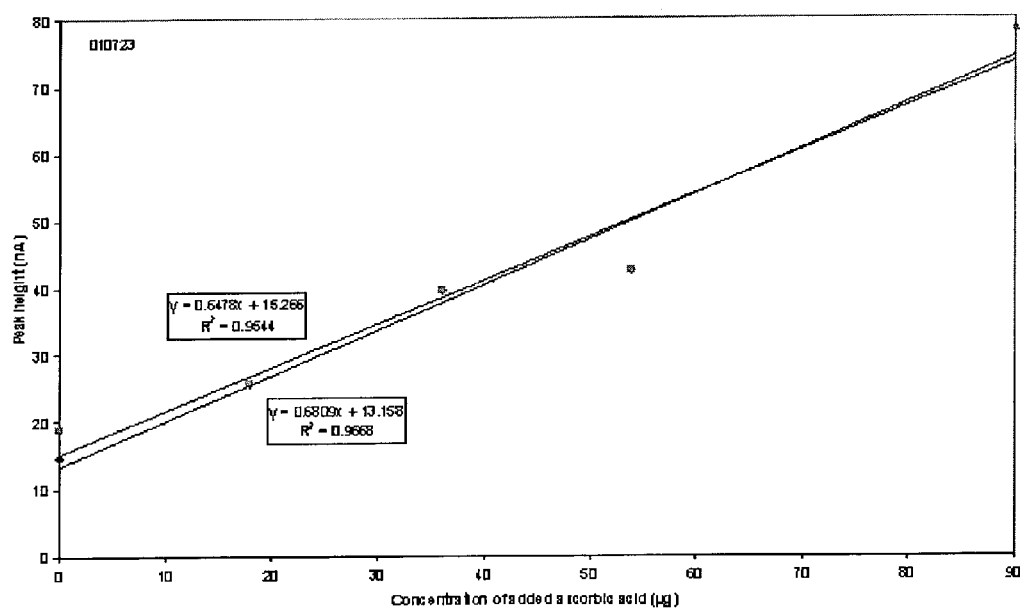
FIG. 10: shows a calibration curve of peak height versus concentration of ascorbate in pureed spinach.

FIG. 10 shows data of peak height versus ascorbate of spiked tomato extract LS voltammetry.

EXAMPLE 6

Analysis of Ascorbate and GSH in Pureed Spinach

Fresh spinach (25 g) was mechanically blended with R.O. water (50 ml) and then frozen to −24° C. in 1 ml aliquots. Individual portions were thawed for up to 1 hour at room temperature prior to analysis. Puree was then diluted to 100 ml in McIlvaine buffer pH 4. Mixture was stirred prior to analysis. Celullose/nitrocellulose-electrode (D14 for ascorbate; CoPC/D14 for GSH) construct was immersed to a depth of 5 mm in the unstirred spinach/buffer mixture. Voltammetry (linear sweep for AA; differential pulse voltammetry for GSH) was performed when the aqueous mobile front reached to 5 mm before the distal end of the nitrocellulose strip.

Figure 11:
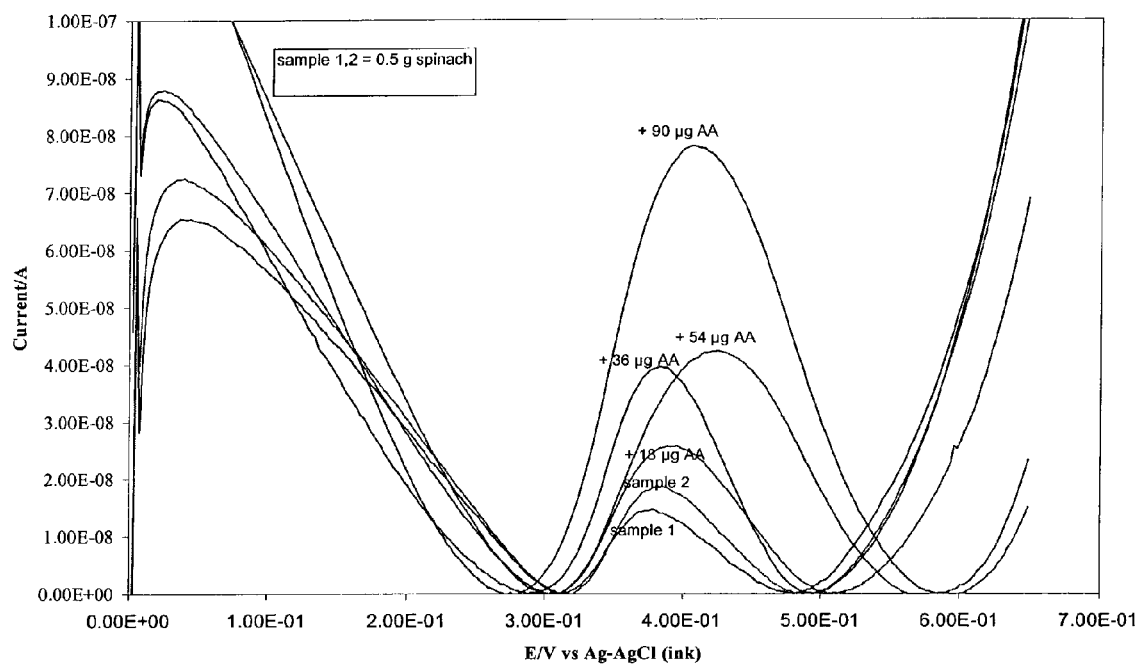
FIG. 11: illustrates an analysis of reduced glutathione in pureed spinach.

Results illustrated in FIG. 11.

The invention claimed is:

1. An electrochemical biosensor for quantifying one or more redox species originally present in a liquid sample comprising a background electrochemical activity, wherein said biosensor does not employ a enzymatic mediator means for detection of the redox species or a wet electrode arrangement and comprises:

i) an electrode system comprising a single working electrode, a counter electrode and a reference electrode, wherein the counter electrode and reference electrode may be optionally combined;

ii) a filter means comprising a sample loading position, said filter means being either directly affixed to and in intimate contact with a charge transfer surface of the working electrode or directly affixed to and in intimate contact with an intermediate layer which is directly affixed to and in intimate contact with the charge transfer surface of the working electrode without an intervening wet electrolyte phase;

wherein said filter means separates said sample loading position from said charge transfer surface by an amount of filter material capable of providing a tangential peak height for said background electrochemical activity of ICSS than 30% of the tangential peak height for said redox species; and wherein the redox species originally present in the liquid sample is quantified by direct electrochemical reaction with the charge transfer surface of the working electrode and is not generated by an enzymatic mediator during the measurement process.

2. The electrochemical biosensor of claim 1, wherein said filter material is selected from the group comprising synthetic membranes, nitrocellulose, cellulose, silica, filter paper and agar gel.

3. The electrochemical biosensor of claim 2, wherein said intermediate layer comprises cellulose.

4. The electrochemical biosensor of claim 1, wherein said biosensor comprises a means for measuring an electrochemical signal.

5. The electrochemical biosensor of claim 1, comprising a means for directing the usage of said biosensor within one or more predetermined parameters for quantification of said one or more redox species.

6. The electrochemical biosensor according to claim 1 wherein the working electrode comprises a dried carbon ink in intimate contact with the filter means.

7. The biosensor according to claim 1 wherein the biosensor system is designed for a single use and is disposable.

8. The biosensor according to claim 1 further comprising a potentiostate built into the biosensor to form a disposable device provided to consumers.

9. A method of using an electrochemical biosensor for quantifying one or more redox species in a liquid sample comprising a background electrochemical activity, wherein said method does not employ a enzymatic mediator means for detection of the redox species or a wet electrode arrangement and comprises the steps of
   (a) providing an electrochemical biosensor which comprises:
      i) an electrode system comprising a single working electrode, a counter electrode and a reference electrode, wherein the counter electrode and reference electrode may be optionally combined;
      ii) a filter means comprising a sample loading position, said filter means being either directly affixed to and in intimate contact with a charge transfer surface of the working electrode or directly affixed to and in intimate contact with an intermediate layer which is directly affixed to and in intimate contact with the charge transfer surface of the working electrode without an intervening wet electrolyte phase;
      wherein said filter means separates said sample loading position from said charge transfer surface by an amount of filter material capable of providing a tangential peak height for said background electrochemical activity of less than 30% of the tangential peak height for said redox species; and
      wherein the redox species originally present in the liquid sample directly reacts electrochemically with the charge transfer surface of the working electrode and is not generated by an enzymatic mediator during the measurement process;
   (b) contacting the sample loading position with said liquid sample; and
   (c) detecting a voltametric change in said electrode system to quantify said redox species.

10. The method of claim 9, wherein said redox species is either ascorbate or reduced glutathione.

11. The method according to claim 9 where in the biosensor in designed for a single use and is disposable.

* * * * *